United States Patent
Nierle et al.

(10) Patent No.: US 10,292,945 B2
(45) Date of Patent: May 21, 2019

(54) DRESSINGS THAT CONTAIN ACTIVE SUBSTANCE

(75) Inventors: Jens Nierle, Hamburg (DE); Karl-Heinz Woeller, Hamburg (DE); Maxi Zier, Eutin (DE); Gerd Mueller, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 782 days.

(21) Appl. No.: 14/241,166

(22) PCT Filed: Aug. 29, 2012

(86) PCT No.: PCT/EP2012/066768
§ 371 (c)(1),
(2), (4) Date: Jun. 16, 2014

(87) PCT Pub. No.: WO2013/030227
PCT Pub. Date: Mar. 7, 2013

(65) Prior Publication Data
US 2014/0308338 A1     Oct. 16, 2014

(30) Foreign Application Priority Data
Aug. 30, 2011   (DE) .......... 10 2011 081 818

(51) Int. Cl.
| | | |
|---|---|---|
| A61F 13/02 | (2006.01) | |
| A61K 9/70 | (2006.01) | |
| A61L 15/58 | (2006.01) | |
| A61K 31/085 | (2006.01) | |
| A61K 31/165 | (2006.01) | |
| A61K 31/205 | (2006.01) | |
| A61K 31/522 | (2006.01) | |
| A61F 13/00 | (2006.01) | |

(52) U.S. Cl.
CPC .......... *A61K 31/085* (2013.01); *A61F 13/025* (2013.01); *A61K 9/703* (2013.01); *A61K 9/7053* (2013.01); *A61K 9/7061* (2013.01); *A61K 9/7092* (2013.01); *A61K 31/165* (2013.01); *A61K 31/205* (2013.01); *A61K 31/522* (2013.01); *A61F 2013/0077* (2013.01); *A61F 2013/00906* (2013.01)

(58) Field of Classification Search
None
See application file for complete search history.

(56) References Cited

U.S. PATENT DOCUMENTS

| | | | |
|---|---|---|---|
| 5,861,348 A | 1/1999 | Kase | |
| 5,921,948 A * | 7/1999 | Kawaguchi et al. | ........... 602/52 |
| 6,143,317 A | 11/2000 | Himmelsbach et al. | |
| 6,488,958 B1 | 12/2002 | Himmelsbach et al. | |
| 6,656,491 B1 | 12/2003 | Brosck et al. | |
| 6,703,043 B1 | 3/2004 | Himmelsbach et al. | |
| 7,001,613 B2 | 2/2006 | Radloff et al. | |
| 8,101,216 B2 | 1/2012 | Jaspers et al. | |
| 2002/0058068 A1* | 5/2002 | Houze | .......... A61K 8/0208 424/487 |
| 2004/0009215 A1 | 1/2004 | Radloff et al. | |
| 2006/0269500 A1* | 11/2006 | Riemer | .......... A61K 8/345 424/70.12 |
| 2008/0038300 A1 | 2/2008 | Jaspers et al. | |
| 2009/0182256 A1 | 7/2009 | Lin | |
| 2010/0298747 A1 | 11/2010 | Quinn | |
| 2010/0312160 A1* | 12/2010 | Creighton | .......... A61F 13/10 602/62 |
| 2012/0089105 A1 | 4/2012 | Jaspers et al. | |

FOREIGN PATENT DOCUMENTS

| | | |
|---|---|---|
| AU | 199925217 B2 | 8/1999 |
| DE | 19650471 A1 | 6/1998 |
| DE | 19749467 A1 | 5/1999 |
| DE | 19804604 A1 | 8/1999 |
| DE | 19804774 A1 | 8/1999 |
| DE | 19825499 A1 | 12/1999 |
| DE | 10012582 A1 | 9/2001 |
| DE | 10056009 A1 | 5/2002 |
| GB | 781975 A | 8/1957 |
| GB | 1570669 A | 7/1980 |
| GB | 2063102 A | 6/1981 |
| GB | 2425487 A | 11/2006 |
| WO | 2006018340 A2 | 2/2006 |
| WO | 2006120066 A1 | 11/2006 |

OTHER PUBLICATIONS

Crawford, HowStuffWorks.com. <http://science.howstuffworks.com/kinesiology-tape.htm>, May 9, 2011, downloaded on May 3, 2016, pp. 1-9.*

* cited by examiner

*Primary Examiner* — Abigail Vanhorn
(74) *Attorney, Agent, or Firm* — Abel Schillinger, LLP (57) ABSTRACT

A dressing for applying to the skin is characterized in that the adhesive mass is applied discontinuously in a strip or wave and contains an active substance.

22 Claims, 4 Drawing Sheets

DRESSINGS THAT CONTAIN ACTIVE SUBSTANCE

BACKGROUND OF THE INVENTION

1. Field of the Invention

The self-adhesive dressings comprise support material that is stretchable and reboundable in one direction, onto which adhesive masses are applied, in stripe form and/or wave form, crossways relative to the stretching direction, said adhesive masses comprising one or more active substances.

2. Discussion of Background Information

Warming products have for many years played an important role in the treatment of muscular pain. For example, since 1928 there has been the ABC Plaster® with capsaicinoids as active substances. Besides this plaster, there are various other products on the market which use active substances with capsaicinoids or derivatives thereof.

The mode of action of these products is based firstly on the promotion of circulation in the affected areas and secondly on the influence on the metabolism. Thus, for example, capsaicin stimulates the release of substance P, a neuropeptide made of eleven amino acids. This molecule actively intervenes in the pain cycle and contributes to a reduction in perceived pain.

Cellulite (medical term: Dermopanniculosis) is not a disease, but a cosmetic problem.

The causes of cellulite lie primarily in the specific structure of the female skin and the reaction to female hormones. Fat cells are stored in the subcutaneous skin. The amount of these is established as early on as in the infant stage and cannot be influenced by nutrition or sport. In the fat cells, the fatty acids from food are converted to fats and are incorporated in nodular form in connective tissue. If these fats are not broken down over a prolonged period (e.g. sport), and if the body is additionally overnourished, the cells can expand to many times their size. The increased cells then squeeze through the connective tissue, resulting in the dreaded orange peel, also known as cellulite.

Other consequences in old age are spider veins, varicose veins, thromboses and leg ailments. Often, the thighs are also storage for excess fat that is absorbed via the diet. The unsightly, lateral thickenings of the thigh, also called saddlebags, combined with cellulite, is often a great worry for those affected.

An annoying cosmetic phenomenon is marks in the skin following pregnancy, which have a detrimental effect on the aesthetic appearance. So-called stretch marks are also called striae or pregnancy stretch marks. These too are not necessarily a disease, but a purely cosmetic problem.

Skin stretch marks (striae) are cracks in the subcutaneous tissue. They are formed on the stomach, hips or breasts. Striae are firstly bluish-red, later yellowish-white. They have a similar appearance to scars. They are formed when the skin is overstretched and also the ability of the skin to stretch has decreased. A high cortisone level promotes the formation of stretch marks. This hormone allows the skin to retain more water and it reduces the elasticity of the skin.

If the skin becomes stretched as a result of pregnancy or weight gain, small cracks are formed in the elastic tissue. The skin becomes thinner at the points affected and the blood vessels show through with a bluish color. Later, the areas heal and the marks become white. Unfortunately, the marks cannot be expected to disappear. Pregnant women, people in puberty, athletes, people receiving hormone treatment and people with increased body weight are the groups of people predominantly affected by striae.

In pregnancy, the cortisone level in the blood is increased. For many women, stretch marks appear in the belly skin. These are called "striae gravidarum" or pregnancy stretch marks.

If stretch marks are present, to current knowledge, they can no longer be completely reduced. However, a reduction and alleviation up to 50% is possible. It is also the case for laser treatments that they do not have the desired success in most cases.

It is therefore an object of the present invention to provide a dressing which permits a treatment of the areas of skin affected by striae and cellulite and brings about a cosmetic improvement in these skin areas.

DE 10056009 A1 discloses matrix plasters containing active substance for the controlled release of hyperemic active substances.

DE 19650471 A1 describes plasters containing active substance with a support material and a hot-melt adhesive mass applied thereto which comprises at least one hyperemic active substance. The adhesive mass can be applied over the whole area or to parts, the latter in order to improve the air and water vapor permeability. The document is silent regarding stretchability, kinesio or special adhesive mass coatings.

DE 19749467 A1 describes plasters containing active substance with a support material and a hot-melt adhesive mass applied thereto which comprises at least one active substance, where the adhesive mass is foamed.

It is also mentioned that no displacement of dressings results on account of the foamed adhesive mass.

DE 19804604 A1 discloses devices for releasing substances, where the devices comprises an adhesive mass with SEPS (styrene-ethylene-propylene-styrene) block copolymers. The document is silent regarding stretchability, kinesio or special adhesive mass coatings.

DE 19804774 A1 discloses support materials for medical purposes, where the support material comprises a nonwoven fabric oversewn by means of sewing threads and having a maximum tensile strength of at least 10 N/cm. The adhesive mass applied to the support can include active substances. The support material generates a compressive force of 0.2 to 10 N/cm at an elongation of 20 to 70%.

DE 19825499 A1 discloses plasters containing active substance, where the adhesive mass is applied in the form of spun fibers or threads, also in random form.

DE 10012582 A1 describes a method for applying adhesive mass to support materials, where the application takes place in wave form in the direction of the longitudinal direction of the support.

Besides the classic pain preparations, active-substance-free treatment methods such as, for example, kinesio, have become established in recent years.

U.S. Pat. No. 5,861,348 describes and claims kinesio therapy for the first time. Of importance and the basis here is the wave-like application of an adhesive mass without active substance influence.

Here, the treatment effect is primarily based on a mechanical effect. The skin area to be treated is subjected to a certain pretensioning and then stuck with a stripe of the elastic kinesio tape. If the skin of the treated area now relaxes, the tape makes folds which are oriented crossways to the direction of travel of the tape. As a result of the combination of these folds with the normal movements of the skin, a constant stimulatory effect is exerted on the area in question, and this has a positive influence on muscle tension and/or pain.

The adhesion of the tape to the skin and the mechanical displacement triggered as a result during performed body movements results in a stimulation of the mechanoreceptors in the skin. This results in pain suppression at a direct spinal level. The prior art relating to kinesio points to no adhesives of any kind or similar substances which can trigger intolerances or allergies in many cases being present in the tape used.

Similarly, there are no kinds of active substances (drugs) in the support materials and adhesive masses and thus adversely affect neither medicamentous nor homeopathic treatments carried out in parallel.

For example, a kinesio tape is known under the brand ChiroTape®. Herein, wave-like raising of the skin lead to a pressure reduction in the tissue as a result of an increase in space between skin and musculature. This in turn results in regulation of the lymph and blood circulation.

Kinesio is to be differentiated from pure "taping".

WO 2006/018 340 A2 describes tapes containing active substance for the treatment of joint diseases.

"Taping" is another term for "functional dressing technology". This term describes dressings which help, as a result of partial immobilization of joints, to perform desired movements and to avoid other (painful) movements. The term is derived from the American term "tape" for dressing plasters.

Taping on the one hand aims to imitate the capsular ligament structures and, in doing so, achieve a selective support and stabilization, and on the other hand to also attain a promoting effect on the healing process by tape dressings constantly leading to tensile and pressure loadings of superficial and deeper muscle areas. This increases tension and circulation in these muscle areas; the rate of healing is increased, and muscle loss is avoided. The muscle pump can furthermore provide for the removal of metabolic products through veins and lymph vessels. In the joints, the cartilage is restored to its function as a result of the furthermore possible stressing and destressing.

Taping is nowadays a care method for the prophylaxis and treatment of injuries, diseases and changes to the locomotor apparatus that has proven successful for many years and been documented by numerous investigations. It assists, protects and deburdens a functional unit, but is not a substitute for total immobilization, but is rather indicated by a targeted immobilization only of the injured structure for all injuries or changes that do not require complete immobilization.

The actual tape dressing here is applied in stripes of preferably inelastic self-adhesive bands, so-called reins, or in connection with self-adhesive bands with a short elasticity of extension. It protects, supports and relieves vulnerable, damaged or defective parts of a functional unit. It permits selective strain in the pain-free sphere of movement, but prevents extreme or painful movements.

The application of such dressings requires expert skill and experience and can therefore not usually be carried out by lay persons without taping experience.

Taping is completely different to kinesio therapy from the underlying physiological orientation and mode of action. In contrast to this, in kinesio, no type of immobilization is exercised; complete mobility of the taped area is entirely retained in the case of the kinesio therapy.

What the two therapy forms do have in common, though, is that they dispense with active substances.

Nevertheless, it is desirable to combine kinesio with the advantages of an active substance treatment.

Furthermore, it is desirable in particular to combine heat treatment with kinesio so as to increase the effect of the constant stimulatory effect on the skin.

SUMMARY OF THE INVENTION

The invention is a self-adhesive dressing comprising a support material that is stretchable and reboundable only in one direction. An adhesive mass is applied to the support. The adhesive mass comprises one or more active ingredients, where the adhesive mass is not applied to the whole area, but in stripe form or wave form which runs crossways to the stretchability direction of the support material.

Not over the whole area means that the percentage fraction of support surface coated with adhesive mass is at most 95%, in particular between 20 and 70%, preferably 40 to 60%.

BRIEF DESCRIPTION OF THE DRAWINGS

In the drawings:

FIGS. 2.1 to 2.5 show various geometric forms which the dressing of the invention may take.

DETAILED DESCRIPTION OF THE INVENTION

Figure 1:
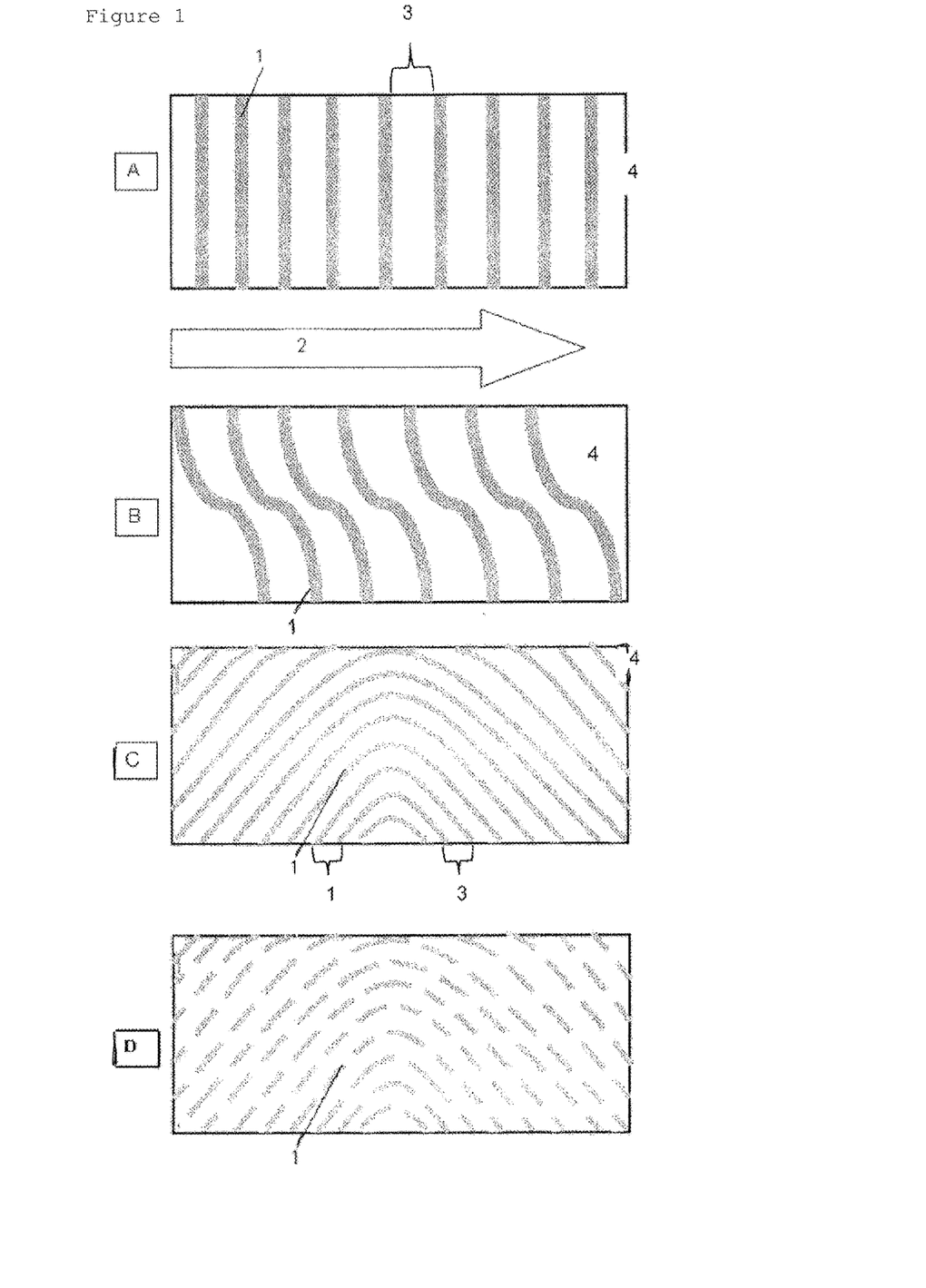
FIGS. 1A-G show various stripe or wave forms in which the adhesive mass may be applied to the support.

The uncoated regions ((3) in FIG. 1) can vary individually as a result of the application of adhesive mass. The kinesio active substance application according to the invention thus allows an increase or decrease in the wave-like raising of the skin between the uncoated regions, depending on the intended use. The dressing according to the invention combines the mechanical effects of kinesio with the biochemical effects of the active substance.

The adhesive mass of the kinesio-active substance dressing according to the invention is applied to the side of the support such that, upon applying the dressing, the adhesive mass can make contact with the skin.

The adhesive mass is advantageously not foamed on account of the kinesio application requirement.

In a preferred embodiment, the adhesive mass is solvent-containing.

As an alternative preferred embodiment, however, a solvent-free hot melt adhesive mass can also be used. In this embodiment, the hot-melt adhesive, which is doped with an active substance, can be applied continuously with the help of a screen printing process, or an intaglio roll into which the pattern to be applied is incorporated. It is also conceivable to apply the hot-melt adhesive in a discontinuous process by means of a number of separate nozzles arranged in the pattern to be applied. The hot melt process is suitable in particular for line patterns which differ from a simple, sinusoidal line image.

Preferred support materials for self-adhesive dressings according to the invention have a stretchability of from 110 to 200%, particularly preferably 120 to 160% and very particularly preferably 130 to 140% stretchability.

Within the context of the invention, stretchability refers to the longitudinal direction, with the material being largely unstretchable in the transverse direction. The support material is stretchable in a direction if a 25% stretching is brought about in the longitudinal direction upon applying a force of from 0.05 to 0.5 N/cm, particularly preferably from 0.1-0.3 N/cm.

Unstretchable means that a 25% strength stretching is achieved in the transverse direction only above a force of 80 N/cm, preferably above 100 N/cm.

The support material is stretchable and reboundable in one direction, with the stretch- or wave-like adhesive mass application according to the invention being understood to be transverse to this direction.

The stretchability is the relative change in length (lengthening or shortening) of the support under stress, for example as a result of the motivity. If the dimension of the support increases, then this is a positive stretching (elongation), otherwise it is a negative stretching or compression.

The stretching (elongation) of the supports according to the invention is 110 to 200%, i.e. they can be extended to twice their length without tearing.

Reboundability means that the stretched materials return to their starting position, with return to the starting state being complete or partial depending on the material.

Ideally, complete rebounding to the initial state takes place following elongation and discontinuation of the acting forces on the support material.

The preferred support material here is composed of a natural fiber, such as cotton, wool or a chemically modified natural fiber, such as e.g. viscose. In order to ensure the stretchability or reboundability of the support, and if the fabric on its own does not have the required stretching properties, the fabric of the support preferably additionally comprises one or more elastic threads which are woven into the stretchable direction of the material. This thread can consist e.g. of elastane or rubber. Wherein the elastic thread can optionally be configured with or without a coating (by a thread e.g. made of natural fiber). The thread counts of the fabric fluctuate in the warp and weft direction in the range from 8-30 threads per cm. Particularly preferably, the thread counts in the weft direction are between 15 and 28 and in the warp direction between 10 and 20. Very particularly preferably, the thread counts in the weft direction are between 20 and 26 and in the warp direction between 12 and 16. The areal weight of the support materials here is usually in the range of 140-200 $g/m^2$, preferably in the range of 150-190 $g/m^2$, particularly preferably in the range of 170-185 $g/m^2$.

Self-adhesive dressings according to the invention can be used either as rolled goods as well as precut individual dressings, so called pre-cuts. For both embodiments, it is advantageous if the self-adhesive dressings are laminated or adhered with a certain pretension of 110 to 160%, preferably 110 to 130%, onto the release paper or the release film, or in the case of corresponding rolled goods onto their own back.

Pre-cuts can be preshaped for adaptation to any anatomical actuality. The product geometries in this connection may be round, oval, square, regular and irregular or be made from combinations thereof. In particular embodiments, pre-cuts can also be made three-dimensional by corresponding changes in the layer thickness (see FIG. 2).

In the preferred stripe form, pre-cuts have a maximum product width of 2 to 20 cm, preferably 4 to 6 cm, and a maximum product length of 2 to 100 cm, preferably 5 to 30 cm, particularly preferably 15 to 20 cm or 5-15 cm.

Rolled goods of self-adhesive dressings according to the invention likewise have a maximum product width of 2 to 20 cm, preferably 4 to 6 cm, and a product length, wound into a roll, of 3 to 20 m, preferably 5 to 10 m.

The dressing is applied with the adhesive side to a release material, which advantageously has a lower stretchability than the dressing, and is wound up in the form of a roll. During use, an individual length can thus be cut from the roll. For use, lengths as required can be shortened by the user himself, as illustrated in the figures.

In a preferred embodiment, both the precuts and the rolled goods are not per se self-adhesive, as is customary with classic tapes, but equipped with a release material which faces towards the side coated with adhesive material and protects this. The release material is preferably a release paper which is coated at least on one side with silicone or fluorocarbons, or a release film.

The hydrophobicization of the support on the upper surface that is often applicable for rolled-up plasters and adhesive bands, can be dispensed with in this preferred form according to the invention of the dressing with release material, release liner. The hydrophobicization serves here to avoid it from sticking to itself during rolling. According to the invention, however, a release material (release paper, release layer (release liner)) is preferably inserted between adhesive layer and support upper side, meaning that no adhesion can take place during rolling.

The stretchability of the release material is advantageously less than that of the support and can therefore not be easily removed during use. On account of the different stretching behavior of the support and the release liner, the trained practitioner can rip this and better remove it.

In a further embodiment, for easier handling, the dressing can be provided with a support material that can be torn crossways to the direction of travel. As a result, the tape can also be used without the help of scissors.

Figure 2:
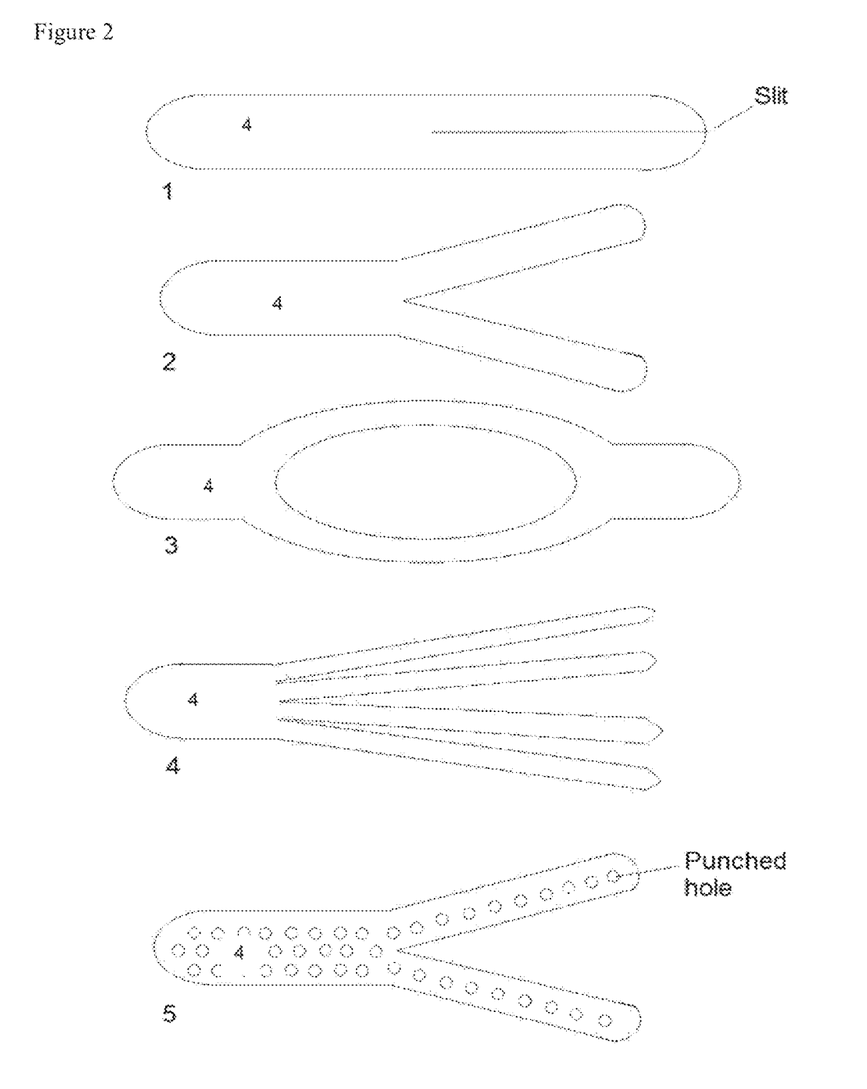

FIG. 2 shows preferred embodiments, with FIG. 2.1 showing a dressing (4) for use on arms, legs, shoulders and backs with a slit, FIG. 2.2 showing a dressing (4) for use on arms, legs, shoulders and backs, FIG. 2.3 showing a dressing (4) for use on joints, e.g. knees, and FIG. 2.4 showing a dressing (4) for use on arms, legs, shoulders and backs.

The dressing (4) can furthermore be provided with punched holes, as shown in FIG. 2.5. As a result of this, an additional stimulus is exerted on the treated skin areas at the edges of the holes. The holes are in this case arranged in several straight lines in the longitudinal direction of the tape. The hole size here can vary between 3 mm and 8 mm. The distance between the holes is between 1 cm and 2 centimeters.

It is the subject matter of the present invention to increase the positive effect of products such as kinesio through the use of an in particular hyperemic active substance.

The circulation-promoting preferred substances described in Table 1 can contribute to removing metabolic products which have accumulated in the muscles e.g. as a result of tension and hinder the healing process. Furthermore, the release of substance P is suppressed by e.g. capsaicinoids, which additionally alleviates pain.

In this connection, it was surprisingly found that the circulation-promoting effect of the capsaicinoids is not necessarily required, but that even in the case of active substances which only exert a stimulatory effect on the nerves in question, an increase in the positive kinesio-taping effect can already be achieved.

The active substances of the dressing according to the invention are therefore not limited to capsaicinoids. The use of substances which promote circulation, such as e.g. nicotinic acid derivatives, is advantageous. The active substances listed in the table below have proven to be particularly advantageous in the combination according to the invention of heat and kinesio therapy.

TABLE 1

Circulation-promoting active substances

Capsaicinoids (0.01-0.20%)
Nonivamide (0.01-0.15%)
Vanilyl butyl ether (0.5-2.5%)
Benzyl nicotinate (0.5-4.0%)
Rosemary oil (0.5-5.0%)
Capsiates (vanillic acid esters) (0.5-2.5%)
Mustard oils (0.2-4.0%)

The aforementioned preferred use concentrations in percent by weight refer here in each case to the total mass content in the applied adhesive mass.

Capsaicin and nonivamide are known active substances in plasters with a local, circulation-promoting effect. On account of their use on the locomotive apparatus, they must as a rule exhibit strong adhesion.

The adhesive force of the kinesio active substance dressings according to the invention has also proven to be advantageous on the skin, which, for example, leads to the dressing being durable for several days on the patient.

For example, active substances such as vanilyl butyl ether, the circulation-promoting effect of which is rather weak, nevertheless exhibit a stimulatory effect on the receptors for heat and pain sensation. In the case of capsaicin, this stimulatory effect manifests itself in a warming to burning feeling. This stimulation counteracts the pain stimulus as a result of the e.g. tension of the musculature, and leads to its reduction.

Particularly preferred active substances to be selected are hyperemic active substances, in particular active substances from the group of the vanilyl alcohol derivatives, such e.g. capsaicinoids or ethers and esters of vanilyl alcohol.

Menthol, camphor and derivatives thereof, but also other essential oils lower the stimulatory threshold of the neuronal cold receptors and thus bring about a feeling of cold. However, they often simultaneously bring about an increase in circulation which, on the contrary, brings about a warm feeling. In a preferred embodiment, these active substances can also be used.

Further active substances to be used according to the invention are to be selected from the group of non-warming, anti-inflammatory active substances from the range of non-steroidal anti-inflammatory drugs (NSAIDs). In particular, these are aspirin (acetylsalicylic acid), diflunisal, salsalate, ibuprofen, etofenamate, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, licofelone, lysine clonixinate, hyperforin and/or figwort. Preference is given here to ibuprofen, diclofenac and salts thereof, indomethacin, flurbiprofen and etofenamat. Here, the kinesio pain treatment can be combined with inflammation- and therefore also pain-alleviating medicamentous treatment, in which case the use concentration in weight fractions of the active ingredients in the applied adhesive mass is preferably between 0.01% and 20%, in particular between 0.5 and 10%.

It is furthermore possible and preferred to also use local pain-suppressing active substances (local anesthetics), such as lidocaine, mepivacaine, prilocaine, articaine, bupivacaine, ropivacaine, etidocaine, dyclonine, procaine, benzocaine, 2-chloroprocaine, oxybuprocaine, tetracaine, fomocaine and their respective derivatives and salts. Preference is given in particular to lidocaine, prilocaine and benzocaine, and the respective derivatives/salts. Here, the kinesio pain therapy can be combined with local anesthetic treatment, in which case the use concentration in weight fractions of the active substances in the applied adhesive mass is then between 0.01% and 10%, preferably between 0.3 and 4%.

Moreover, it is likewise possible to use odor-neutral and/or cosmetic active ingredients. This group includes inter alia cyclohexanecarboxamides (INCI: Menthane Carboxamide Ethylpyridine) and 3-((5-methyl-2-(1-methylethyl)cyclohexyl)oxy)-1,2-propanediol (INCE Menthoxypropanediol).

Further preferred active substances are to be selected from the group carnitine or its derivatives, caffeine and capsaicin, in particular two or all three of these active substances.

The ratio of carnitine or its derivatives to capsaicin and/or caffeine is, according to the invention, preferably in a ratio of from 1 to 100:1, advantageously 1:1. I.e. for a preferred fraction of carnitine of 0.5% by weight, a fraction of 0.5% by weight of caffeine has proven to be extremely effective. Accordingly, a ratio of carnitine, for example of 0.5% by weight to caffeine at 0.3% by weight and capsaicin at 0.2% by weight, is likewise advantageous.

In a further embodiment, the adhesive mass of the dressing can be doped with skin care substances, such as e.g. plant oils, jojoba, aloe vera, or liccochalcone A or dexpanthenol etc. The advantage of such an embodiment is that skin irritations, such as redness etc., can be prevented, but at least lessened, by the added care substances. This is useful particularly on account of the long wearing times of the kinesio dressing.

Preferably, the adhesive mass comprises more than one active substance, preferably two or three, in particular one active substance selected from the group of skin care substances and one or two active substances selected from the group of circulation-promoting substances.

The active substance or substances are preferably present in a fraction of from 0.01 to 20% by weight, based on the total mass of the adhesive mass.

Where restrictions are made to preferred fraction ranges of one or more ingredients, such as active substances, and/or restrictions to certain ingredients, then the preferred fraction ranges then also relate to the selected ingredients.

The active substances are preferably distributed in the adhesive mass in a thermohomogenizer, such as for example thermomixer, thermokneader, roll mill or screw systems. The active substance can be added to the fully produced adhesive mass. By way of example, the adhesive substance can also be incorporated into an intermediate or into the starting mixture.

As well as adhesive cosmetic/medical plasters or matrices, the term dressing also encompasses all cosmetic/medically applicable coverings such as patch, pad, tapes, wipes, supports, dressings, cataplasms, bandages and/or masks.

Self-adhesive here means that the dressing adheres to the skin by virtue of the adhesive mass and does not have to be attached by means of additional fixing devices or compositions.

Kinesio tapes of the prior art are normally provided with acrylate adhesive compositions. Acrylate adhesive compositions are characterized by a very low allergenic potential. Moreover, they are pervious to steam, which means that the moisture which collects under the dressing can evaporate. This fact favors long application times extending to one week since a moisture film, which is injurious to the adhesive force, is no longer able to form between the skin and the adhesive composition.

Adhesive compositions according to the invention are advantageously solvent-based acrylate-based systems which do not require additional crosslinking by means of processes based on electromagnetic radiation. One exception is systems which can be crosslinked by means of infrared radiation. The problem that arises when crosslinking acrylate systems with e.g. UV radiation consists in the free radicals that are formed. These highly reactive particles can enter into chemical reactions with active substance molecules, as a result of which said molecules are either completely destroyed or their physiological effectiveness is at least severely restricted.

The acrylate masses can comprise additional substances such as, for example, adhesive resins, fillers or soluble and insoluble hydrocolloids.

Another way of modifying the adhesive strength of the matrices according to the invention is by adjusting the layer thickness and/or the application amount of the adhesive composition. Per se, the adhesive strength is a material-specific parameter of an adhesive composition and independent of the layer thickness. However, this is only true up to a lower limit of the layer thickness specific for the particular adhesive matrix and below which the adhesive strength can significantly reduce.

The adhesive strength can be measured on polyethylene (PE), as customary in the prior art. Although the values measured in this way are a purely technical description which cannot be transferred 1:1 to people, this thus determined adhesive strength on PE has also proven to be advantageous for the skin since the ability for the patient to keep the tape on for several days was to be determined.

By way of example, the adhesive strengths on polyethylene substrates of a solvent-based acrylate matrix (Gelva 737=vinyl acetate/ethyl acetate) are listed below:

TABLE 2

Adhesive strength on polyethylene substrate

| Application amount of the smear of the adhesive matrix | Adhesive strength on polyethylene substrate |
|---|---|
| 65 g/m$^2$ | 0.722 N/cm |
| 50 g/m$^2$ | 0.500 N/cm |
| 42 g/m$^2$ | 0.490 N/cm |
| 34 g/m$^2$ | 0.351 N/cm |
| 17 g/m$^2$ | 0.341 N/cm |

By adding solubilizers such as oils and esters, it is possible to further modify the adhesive strength and thus to reduce an excessively high adhesive strength. Listed below by way of example upon the addition of 3% decyl oleate (Cetiol V) in a solvent-based acrylate matrix (Gelva 737):

TABLE 3

Adhesive strength on polyethylene substrate with solubilizer

| Application amount of the smear of the adhesive matrix plus 3% Cetiol V | Adhesive strength on polyethylene substrate |
|---|---|
| 34 g/m$^2$ | 0.095 N/cm |
| 17 g/m$^2$ | 0.091 N/cm |

According to the invention, the adhesive strength should be adjusted such that it is (measured on a polyethylene substrate) preferably between 0.3 and 0.8 N/cm, particularly preferably between 0.4 and 0.55 N/cm.

A further preferred type of adhesive compositions of the present invention is based on solvent-based rubber adhesive masses. Particular preference here is given to systems which are based on synthetic rubbers, such as styrene-isoprene-styrene block copolymers or olefin monomers (e.g. isoprene or isobutene). These systems have the advantage that they do not have to be additionally crosslinked, as a result of which the active substances used can be processed in a considerably more gentle manner.

As with the acrylate systems, the rubber-based adhesive compositions can also be admixed with fillers, resins and hydrocolloids.

Preferred adhesive compositions include polyisobutylenes, styrene butadiene rubber, styrene isoprene styrene block copolymers, and optionally additives such as hydrocarbon resins, colophonium glycerol esters and/or pulverulent cellulose.

The use of hydrocolloids in soluble or insoluble form favors a long wearing time of the dressing since the moisture released by the skin can be absorbed and conveyed to the outside of the dressing.

Compared with classic acrylate adhesive compositions, the dressing can, as described, also be coated with rubber adhesive compositions. Compared with many acrylate adhesive compositions, these have the advantage of a more aggressive adhesive behavior, which can significantly prolong the use time of the product.

Preferably, the adhesive composition is also a solvent-free hot-melt adhesive composition.

Furthermore, the use of polyurethane and silicone adhesive compositions is preferred according to the invention.

According to the invention, the adhesive masses are applied in a specific orientation which additionally enhances the mechanical effect of the dressing (4). For example, it is possible to use a straight line (A) or wavy line (B, C) of the adhesive composition (1), which are applied to the support material in the crosswise direction to the stretchability (2) thereof, as shown in FIG. 1.

According to the invention, crosswise direction to the stretchability of the support is to be understood here as meaning that more than 90% of the adhesive composition stripes do not run parallel to the direction of stretching of the support.

90% refers here to the total mass of applied adhesive composition.

In this sense, in FIG. 1C only the wave peaks of the adhesive composition application are considered to be oriented parallel to the direction of stretching of the support. The majority (>90%) of the adhesive composition is applied crossways, i.e. not in parallel (angle 5≠0°) to the direction of stretching of the support. Crossways to the direction of stretching of the support material is understood as meaning all those adhesive compositions stripes or waves whose angles (5) are greater than 5° to the direction of stretching of the support. The fraction of adhesive composition stripes or wave areas which have an angle of 5° or less to the direction of stretching of the support is, according to the invention, less than 10% with regard to the adhesive composition applied overall.

Figure 3:
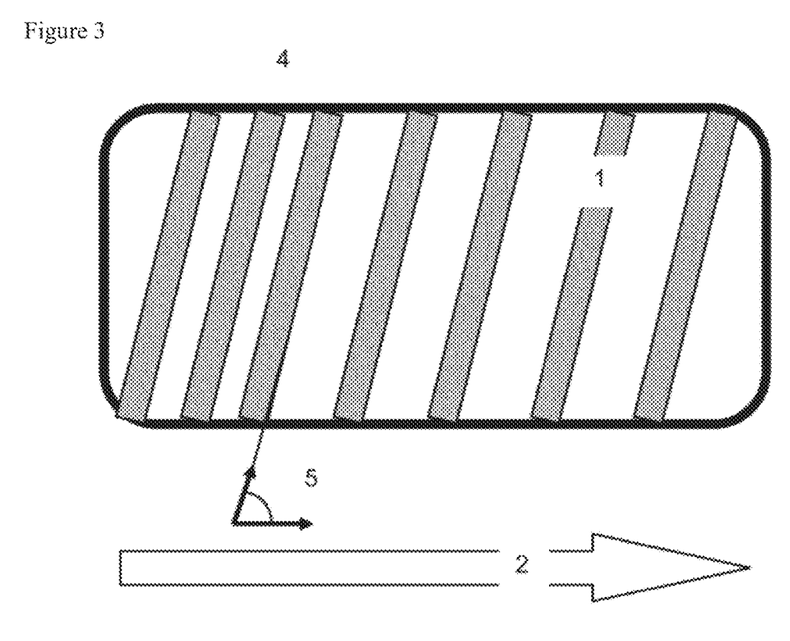
FIG. 3 shows an embodiment of a dressing according to the present invention wherein the adhesive mass is applied on the support in the form of stripes at an angle relative to the stretch of the support.

According to the invention, the adhesive mass is preferably applied in stripe form and the stripes (1) have an angle (5) relative to the direction of stretch of the support (2) in the range from 45° to 90°, in particular 90° (see FIG. 3).

Partial coating of support materials with pressure-sensitive hot-melt adhesives (PSA hot melts) is a known technology whether the hot melt composition is applied for example by means of thermal screen printing, as described for example in DE 42 37 252 A1, or by means of halftone or intaglio printing of webs to be interconnected in the longitudinal or transverse direction (DE 43 08 649 A1). Here, the support material is only partially covered by the adhesive film. Open systems permit good moisture exchange at the open positions of the adhesive film and/or of the support material, i.e. the regions of the support material not covered with adhesive composition.

If a wave-like adhesive composition application is intended, then it is advantageous if the wave coating has an amplitude greater than 20 mm in height. These higher amplitude values compared with the prior art (e.g. DE 10012582 A1) are advantageous for the intended use according to the invention since they lead to greater movements of the skin.

The advantage of the stripe-like or wave-like application of the support material lies in the interrupted adhesive applied to the skin. Temporary skin wrinkles are formed at the positions not coated with adhesive composition and these lead to a type of "micromassage" of the area affected. The skin wrinkles result from a prestretching of the support and the adhesion. As a result of the movement of the body and of the muscles, the adhering parts of the plaster are displaced relative to the nonadhesive parts provided with skin wrinkles. This displacement leads to a lasting stimulus, which continues into the muscle layers beneath the skin. This lasting stimulus contributes significantly to healing. The healing effect, however, is significantly enhanced according to the invention by the active substances used.

The arrangement of the stripes or waves crossways to the direction of stretching also permits for the first time a conveying of moisture since the areas not coated with adhesive composition spread to the edge of the plaster. As well as permitting evaporation through the uncoated parts of the support material, this permits the moisture to be conveyed into regions outside of the area stuck to the dressing because the edges of the dressing are no longer completely "sealed" with adhesive composition.

The conveying of liquids away from the skin surface is ensured by the uncoated regions of the plaster since here a virtually unhindered water vapor permeability is ensured.

Although a grid pattern as an arrangement increases the adhesive strength, it means that the formation of the skin wrinkles described above is restricted. This effect likewise reduces the formation of the described stimulus since at best only punctiform wrinkles can now be formed. However, on account of their geometric shape, these structures can more easily avoid mechanical stress. Moreover, a grid application of the adhesive composition prevents the advantage according to the invention of the liquid conveyance to the edge.

The stripe-like or wave-like adhesive composition application according to the invention crossways relative to the direction of stretching of the support is preferably configured according to the invention such that the region between two adjacent adhesive composition stripes is open to one edge of the dressing (3) (cf. FIG. 1C), preferably to two edges of the dressing (see FIGS. 1A and B).

The release of the active ingredients within the product is advantageously adjusted such that an effect can still be perceived even after a period of 2 days. The delayed effect of the active substances used is achieved here from combination of active substance content and auxiliaries. The release of the active substances can be controlled over a wide time range via the use of e.g. plasticizers and fillers. Examples of such systems are pain patches on the market that contain opiates such as fentanyl, which are applied over several days up to a week and ensure an absolutely uniform release of the active substance over the entire application time. For the determination of the release rate of vanillyl butyl ether (VBE) from e.g. acrylate compositions, it was incorporated into the adhesive compositions in an amount of 0.75% and the release was ascertained over the time in pig skin by means of Franz's cells. Determination of the released amounts into the full-thickness skin was then carried out by HPLC.

TABLE 4

Active substance release VBE

| Acrylate matrix | Percentage release VBE after 24 h |
|---|---|
| Gelva 737 | 2.0 |
| DuroTak 129 | 2.7 |

One possible measure to increase the active ingredient release is the use of solubilizers. According to the invention, preference is given to using decyl oleate (Cetiol V), octyldodecanol and an oil mixture of olive oil, argan oil and shea butter. By adding Cetiol V it was possible to achieve a significant increase in the released amount of VBE in pig skin, at times up to twice the released amount. For the two other additives, lower values were determined, meaning that decyl oleate (Cetiol V) in particular is a preferred solubilizer in the adhesive composition.

TABLE 5

Active substance release of VBE with solubilizer after 24 h

| Acrylate matrix | Percentage release VBE after 24 h |
|---|---|
| Gelva 737 + 3% Cetiol V | 4.0 |
| DuroTak 129 + 3% Cetiol V | 3.5 |

On account of the long wear time of the kinesio dressing of several days, the knowledge of release kinetics over a prolonged period is also decisive. On pig skin, this is not possible due to the natural decomposition processes in the skin, and it was therefore carried out on a silicone film. In this case, each day a sample of the receptor phase was taken from the Franz cell and measured in the HPLC.

TABLE 6

Active substance release of VBE with solubilizer after 7 d

| Acrylate matrix | Percentage release of VBE after 7 d |
|---|---|
| Gelva 737 + 3% Cetiol V | 43.0 |
| DuroTak 129 + 3% Cetiol V | 41.0 |

The relatively high values therefore reveal that the active substance can easily diffuse into the receptor phase through the thin silicone film. The same progress in the release over the application time is evident for both acrylate masses. In the first 24 hours, the release of VBE is highest, and proceeds to a plateau over the time. It is decisive that small amounts are released over the entire time span.

To determine the release rate of capsaicin from an acrylate mass (Gelva 737), Cetiol V was likewise used as solubilizer. For this purpose, 0.355% capsaicin was incorporated into the composition.

TABLE 7

Active substance release of capsaicin after 24 h

| Matrix | Percentage release of capsaicin after 24 h |
|---|---|
| Gelva 737 | 0.4 |

At 0.4%, only relatively little capsaicin penetrates from the Gelva 737 into the skin after 24 hours. As already investigated in the case of VBE, the release over 7 days was also investigated for capsaicin. Here, in addition to the Gelva 737, Duro-Tak 129 was included in the analyses. The table below gives the sums of released capsaicin.

TABLE 8

Active substance release of capsaicin after 7 d

| Matrix | Percentage release of capsaicin after 7 d |
|---|---|
| Gelva 737 | 37.0 |
| DuroTak 129 | 31.0 |

The acrylate masses with one another exhibit a very similar course, and so both masses have proven to be suitable as regards capsaicin release. As already in the case of VBE, here too active substance is released in small amounts over the entire time period.

The dressings according to the invention can be used for the combined active ingredient therapy and kinesio therapy in joint, muscle and/or skin treatment, either therapeutically or nontherapeutically.

Joint, muscle and/or skin treatment in this connection is in particular the physiotherapeutic treatment of the human skeleton, musculature and skin areas.

As therapeutic method, the dressings are to be used for producing a treatment means for treating the human skeleton, musculature and skin areas.

The examples below illustrate the self-adhesive dressings according to the invention.

EXAMPLE 1

53.04 g of Oppanol B80, 106.08 g of Oppanol B10 SFN, 53.04 g of SBR 1011AC, 79.56 g of Vector 4113 and 2.64 g of Lowinox 22 M 46 in 500 g of benzine (70-90° C.) are charged to a dispenser. The mixture is dispersed for 3 hours at room temperature at 2500 rpm and then left to stand overnight. On the next day, a further 100 g of benzine (70-90° C.) are added, and 98.10 g of Regalite 7100 and 100.74 g of Staybelite Ester 10 are added. The mixture is then dispersed for 2.5 hours at room temperature at a rotational speed of 2500 rpm. Then, 21.24 g of Vitacel L600/30 are added and the mixture is dispersed for a further 1.5 hours at 2500 rpm at room temperature Finally, 79.56 g of shea butter and 6.00 g of vanilyl butyl ether are added. The adhesive composition is dispersed at 2500 rpm for a further 30 min.

The adhesive composition obtained in this way is then spread onto a support material in stripe form using a standard commercial spreading device and dried.

EXAMPLE 2

20.00 g of Oppanol B80 are charged to a Z-blade kneader and kneaded until crumbly at a prerun temperature of 150° C. Then, 53.40 g of Oppanol B10 SFN and 46.00 g of Vector 4113 are added. The mixture is then homogenized for 10 min. After the homogenization phase, 28.00 g of Regalite 7100 and 12.60 g of Staybelite Ester 10 are added. This is followed by a homogenization phase of 150 min at a prerun temperature of 100° C. 8.00 g of Vitacel L600/30 are added to the mixture obtained in this way and homogenized over a period of 120 min. Finally, 12.50 g of olive oil, 6.00 g of argan oil, 12.40 g of shea butter and 0.10 g of capsaicin are added. The mixture is homogenized for further 60 min at a prerun temperature of 90° C.

The finished adhesive composition is then squeezed using a hydraulic press at 90° C. and a pressure of 200 bar. The support is then laminated on.

For industrial routine production, the formulation can also be produced by means of extruders and/or be applied to a substrate via conveying screws and slot dies and then laminated with the support material. However, depending on the machine conditions, the matrix can also firstly be coated onto the support material, cut and rolled up, or laminated with release paper, cut and rolled up.

The stripe or wave line that is advantageous according to the invention can be generated easily here by means of machine adjustable lateral movements of the substrate transverse to the direction of travel.

EXAMPLE 3

A dispenser is charged with 500 g of acrylate adhesive composition (Gelva 737-01 in ethyl acetate) with a solids content of 34%. 0.17 g of capsaicinoids is added to this adhesive composition and the mixture is stirred for a period of 30 min. The adhesive composition is then spread on siliconized paper and, after drying, covered with a suitable support material.

Raw Materials Used and Trade Names:

| | |
|---|---|
| Oppanol B 10 SFN | polyisobutylene |
| Oppanol B 80 | polyisobutylene |
| SBR 1011 AC | styrene butadiene rubber |
| Vector 4113 | styrene isoprene styrene block copolymer |
| Lowinox 22 M 46 | stabilizer (phenol, 2,2'-methylenebis[6(1,1-dimethylethyl)-4-methyl-2,2'-methylenebis(6-t-butyl-4-methylphenol)) |
| Regalite 7100 | hydrocarbon resin (partially hydrogenated hydrocarbon resins) |
| Staybelite Ester 10 | colophonium glycerol ester |
| Vitacel L600/30 | pulverulent cellulose |

What is claimed is:

1. A self-adhesive dressing, wherein the dressing comprises a support that is stretchable and reboundable in only one direction with a stretchability of from 110% to 200%, and an adhesive composition comprising one or more active substances, the adhesive composition being present on the support on only a part of the area thereof and in the form of one or more stripes and/or waves running crossways to a stretchable direction of the support and comprising one or more broken stripes and/or waves.

2. The dressing of claim 1, wherein the adhesive composition is present in a form which comprises broken waves.

3. The dressing of claim 1, wherein the waves have an amplitude of greater than 20 mm in height.

4. The dressing of claim 1, wherein the adhesive composition is present in a form which comprises broken stripes.

5. The dressing of claim 1, wherein the stretchability of the support is from 120% to 160%.

6. The dressing of claim 1, wherein the stretchability of the support is from 130% to 140%.

7. The dressing of claim 1, wherein the dressing further comprises punched holes.

8. The dressing of claim 1, wherein the support comprises a fabric into which one or more elastic threads have been woven in the stretchable direction of the support.

9. The dressing of claim 1, wherein the adhesive composition is a solvent-free hot melt composition.

10. The dressing of claim 1, wherein the one or more active substances comprise vanillyl butyl ether.

11. A self-adhesive dressing, wherein the dressing comprises a support that is stretchable and reboundable in only one direction, and an adhesive composition comprising one or more active substances, the adhesive composition being present on the support on only a part of the area thereof and in a form which comprises one or more waves running crossways to a stretchable direction of the support and comprising broken waves.

12. The dressing of claim 11, wherein the waves have an amplitude of greater than 20 mm in height.

13. The dressing of claim 11, wherein the dressing further comprises punched holes.

14. The dressing of claim 13, wherein the punched holes have a size of from 3 mm to 8 mm.

15. The dressing of claim 11, wherein the support comprises a fabric into which one or more elastic threads have been woven in the stretchable direction of the support.

16. The dressing of claim 11, wherein the adhesive composition is a solvent-free hot melt composition.

17. The dressing of claim 11, wherein the one or more active substances comprise vanillyl butyl ether.

18. The dressing of claim 11, wherein the support that is stretchable and reboundable in only one direction with a stretchability of from 110% to 200%.

19. A self-adhesive dressing, wherein the dressing comprises a support that is stretchable and reboundable in only one direction and comprises holes, and an adhesive composition comprising one or more active substances, the adhesive composition being present on the support on only a part of the area thereof and in the form of one or more stripes and/or waves running crossways to a stretchable direction of the support and comprising one or more broken stripes and/or waves.

20. The dressing of claim 19, wherein the holes are arranged in several straight lines in the stretchable direction of the support.

21. The dressing of claim 20, wherein the holes have a size of from 3 mm to 8 mm.

22. The dressing of claim 21, wherein a distance between the holes is from 1 cm to 2 cm.

* * * * *